(12) United States Patent
Galburt et al.

(10) Patent No.: US 11,906,415 B1
(45) Date of Patent: Feb. 20, 2024

(54) POLLUTANT SENSOR DEVICE, SYSTEM AND METHOD

(71) Applicant: Halo Smart Solutions, Inc., Bay Shore, NY (US)

(72) Inventors: Paul Galburt, Punta Gorda, FL (US); Kenneth Addy, Massapequa, NY (US); Frank L. Jacovino, Northport, NY (US)

(73) Assignee: Halo Smart Solutions, Inc., Bay Shore, NY (US)

( * ) Notice: Subject to any disclaimer, the term of this patent is extended or adjusted under 35 U.S.C. 154(b) by 0 days.

(21) Appl. No.: 17/977,002

(22) Filed: Oct. 31, 2022

(51) Int. Cl.
*G01N 15/06* (2006.01)

(52) U.S. Cl.
CPC ..... *G01N 15/06* (2013.01); *G01N 2015/0693* (2013.01)

(58) Field of Classification Search
CPC ............... G01N 15/06; G01N 2015/0693
See application file for complete search history.

(56) References Cited

U.S. PATENT DOCUMENTS

| | | | |
|---|---|---|---|
| 10,970,985 B2 | 4/2021 | Antar et al. | |
| 11,183,041 B2 | 11/2021 | Antar et al. | |
| 11,302,164 B2 | 4/2022 | Antar et al. | |
| 11,302,165 B2 | 4/2022 | Antar et al. | |
| 11,519,842 B2 * | 12/2022 | Pariseau | G01N 15/1459 |
| 2017/0315105 A1 * | 11/2017 | Takeda | G01N 33/0042 |

FOREIGN PATENT DOCUMENTS

WO  WO-2022162307 A1 * 8/2022

OTHER PUBLICATIONS

English Machine Translation of Mareuge et al, WO 2022/162307 A1 (Year: 2022).*

* cited by examiner

*Primary Examiner* — David Z Huang
(74) *Attorney, Agent, or Firm* — Williams Mullen; Thomas F. Bergert

(57) ABSTRACT

Embodiments of a sensor device, method and system employ one or more particle detection sensors to collect particle measurement values in a plurality of particle bins collecting particles of different sizes, generate a histogram representing the particle measurement values and determine based on a comparison of the histogram with a profile histogram for a pollutant, a match quality indicative of whether the pollutant is present in the environment. In various embodiments, a location of a pollutant is also determined according to the determined match quality.

28 Claims, 10 Drawing Sheets

Fig. 10

| Bin # | PROFILE | S1 | S2 | S3 | S4 | S5 | S6 | S7 | S8 | S9 | S10 | S11 | S12 | S13 | S14 | S15 | S16 | S17 | S18 | S19 | S20 |
|---|---|---|---|---|---|---|---|---|---|---|---|---|---|---|---|---|---|---|---|---|---|
| 1 | | 10 | 9 | 8 | 7 | 6 | 5 | 4 | 3 | 9 | 1 | 0 | 10 | 10 | 10 | 9 | 10 | 10 | 10 | 7 | 10 | 1 |
| 2 | | 9 | 8 | 7 | 6 | 5 | 6 | 3 | 2 | 9 | 9 | 3 | 9 | 8 | 9 | 10 | 9 | 9 | 8 | 7 | 7 | 9 |
| 3 | | 8 | 7 | 6 | 5 | 4 | 7 | 8 | 2 | 9 | 3 | 8 | 8 | 7 | 6 | 8 | 7 | 8 | 8 | 8 | 8 | 8 |
| 4 | | 7 | 6 | 5 | 4 | 3 | 8 | 7 | 1 | 8 | 7 | 4 | 7 | 6 | 5 | 4 | 7 | 7 | 5 | 5 | 6 | 7 |
| 5 | | 7 | 5 | 4 | 3 | 2 | 9 | 6 | 1 | 7 | 8 | 6 | 6 | 7 | 5 | 3 | 5 | 6 | 6 | 6 | 6 | 6 |
| 6 | | 8 | 4 | 3 | 2 | 1 | 6 | 5 | 0 | 6 | 5 | 5 | 6 | 5 | 4 | 3 | 3 | 7 | 4 | 4 | 3 | 5 |
| 7 | | 9 | 3 | 2 | 1 | 0 | 7 | 4 | 0 | 5 | 3 | 6 | 4 | 3 | 4 | 5 | 4 | 4 | 4 | 4 | 4 | 4 |
| Match quality | | 16 | 23 | 30 | 37 | 8 | 15 | 49 | 5 | 19 | 26 | 9 | 17 | 15 | 16 | 13 | 7 | 13 | 17 | 14 | 18 |

POLLUTANT SENSOR DEVICE, SYSTEM AND METHOD

TECHNICAL FIELD

The present disclosure pertains to sensors and, more specifically, to a sensor device, system and method for effectively detecting a pollutant and/or the location of a source of a pollutant.

BACKGROUND AND SUMMARY

Individual sensors exist for things like fire, smoke, carbon monoxide, and carbon dioxide. These devices are generally manufactured as single purpose modules that are qualified for life safety applications and designed to fit into traditional low voltage wired burglar and fire alarm system topologies, for example. These units are designed to be very narrow in scope and react only in terms of a single threshold where the monitored gas or condition passes a known life safety threshold. When that threshold is passed, a simple electrical circuit or audible alarm can be triggered.

Buildings inhabited by humans, particularly institutional buildings like schools or commercial environments, or even residential structures, are also faced with environmental conditions where chemicals or particles make it into the air at levels that may not in themselves be toxic to humans but indicate some sort of activity or occurrence that may either be problematic for a different reason or may be leading up to a situation where actual toxicity might occur. Further, outdoor spaces like entertainment venues for concerts and sporting events face similar environmental conditions.

Such conditions are often caused by human behavior such as, but not limited to, smoking, vaping, sniffing glue solvents, alcohol consumption, and usage of various cleaning products, perhaps in ways unintended by the manufacturer. None of these pollutants have established life safety levels which justify immediate alarms, yet their presence can indicate an overall situation that requires intervention for health, safety, policy or other reason. In addition to the above, it is well known that in stagnant air, larger particles settle more quickly in a predictable time frame and that in turbulent air (e.g., open windows, air conditioners, movement of people, fans, open air environments), the larger particles settle more quickly with an exponential delay.

Recent advances in Mie Scattering particle detection sensors allow particles of various sizes to be measured and to be "binned" into sizes ranging in the nM to 10-micron range, for example. Airborne contaminants in this size range may be due to a pollutant such as smoke from fire, vaping or vape, tobacco or other substance, smoke, including smoking of drugs and gun smoke, bacteria, spores, viruses, dust, fumes, cooking, aerosol products, etc. In all cases, the constituent mix of particles differs depending on the pollutant itself, and the mix of particle sizes changes over time depending on the pollutant, the location, and the environment. For purposes of the present disclosure, the term "vape" or "vaping" may be employed herein to denote the activity of inhaling and/or exhaling the aerosol or "vapor" produced by an e-cigarette or similar device, and "vape" may further be employed to denote the actual gases, aerosols and/or particles from the vaping activity. Further, for purposes of the present disclosure, a "pollutant" can be considered any substance(s), contaminant(s), gas(es), particle(s), dust, fine particulate matter, chemical(s) or other element(s) present in the air or ambient environment that are toxic, hazardous, problematic or otherwise undesirable. According to the present disclosure, vape is an example of a pollutant.

Sensor devices for detecting vaping and other pollutants can be obtained through Halo Smart Solutions, Inc. of Bayshore, New York. Also, such technology is described, for example, in U.S. Pat. Nos. 10,970,985; 11,183,041; 11,302,164 and 11,302,165. Vape detectors and other detectors are, in general, used to enforce "no vaping" rules and to indicate hazardous conditions, but these existing systems typically detect particles of a certain size within a fixed volume (e.g., vape in a school bathroom or an air pollutant such as fine particulate matter (i.e., PM2.5) in a hotel room, or clean room quality). In addition, there are aspirating fire detection systems, but these simple devices look for concentrations of smoke above a certain threshold and do not intelligently consider particulate size mix or the changes of the mix over time. Further, such devices generally cannot pinpoint a location of a source of pollutants in an open area. By way of example, one may employ several vape detectors to cover a large open-plan office area in which there is occasional vaping activity. Such an arrangement may ensure that there would be a vaping alert somewhere in the office area but the location would be poorly defined.

In various embodiments, the system, method and device of the present disclosure employs one or more histograms representing the various particle sizes in sampled air and the change in the histogram(s) shape over time. For example, the larger particles from exhaled vape will settle more quickly than smaller particles and will settle nearer to the person vaping. Similarly, in an industrial environment, the dust created by milling or polishing machinery will settle depending on the pollutant size and distance from the source. By comparing the histograms generated by one or more sensors according to the present disclosure, it is possible to locate the source and/or location of the vaping event and issue an alert or notification to one or more appropriate devices accordingly.

In various embodiments, a vape detector profile histogram for the sensor nearest the origin of the pollutant event would initially show larger particles, declining quickly. A more distant sensor may be unlikely to detect the larger particles and would sense the smaller particles at some time delay after the closer sensor or sensors sense the event. The specific delay is dependent on the local environment. It will be appreciated that embodiments of the present disclosure can detect and localize one or more pollutants in an industrial environment such as factory floors as well as at other venues such as concerts, exhibitions, conferences, etc. where smoking, vaping and generation of other pollutants may be a concern.

In various embodiments, a networked array of sensors is provided and allows accurate detection and location of a pollutant event. The location of the pollutant event can include distance as well as angle. In other embodiments, a single sensor is employed to detect a pollutant and provide a good estimate of distance and/or angle from the sensor to the pollutant. In various embodiments, appropriate training data before or at the time of installation of one or more sensors according to the present disclosure and thereafter during regular operation can facilitate a machine learning process to gradually improve the performance of the system, i.e., the ability of the system to ignore false alarms and to catch hazardous pollutants including vape and smoking policy violations reliably.

Embodiments of the sensor device can incorporate a suite of sensor components that can detect oxidizing gases, reducing gases, ammonia, carbon dioxide-equivalent, volatile organic compounds, nitrous oxide, sound, noise, visible light, humidity, temperature, movement and particulates, for example. In addition, the present disclosure pertains, in part, to a sensor device, method and system providing detection of unwanted activities and optionally with detection of the location of the source of such unwanted activities.

BRIEF DESCRIPTION OF THE DRAWINGS

FIG. 10 is a graph representing match quality values for sensor measurements from various sensors in accordance with embodiments of the present disclosure.

DETAILED DESCRIPTION

Figure 1:
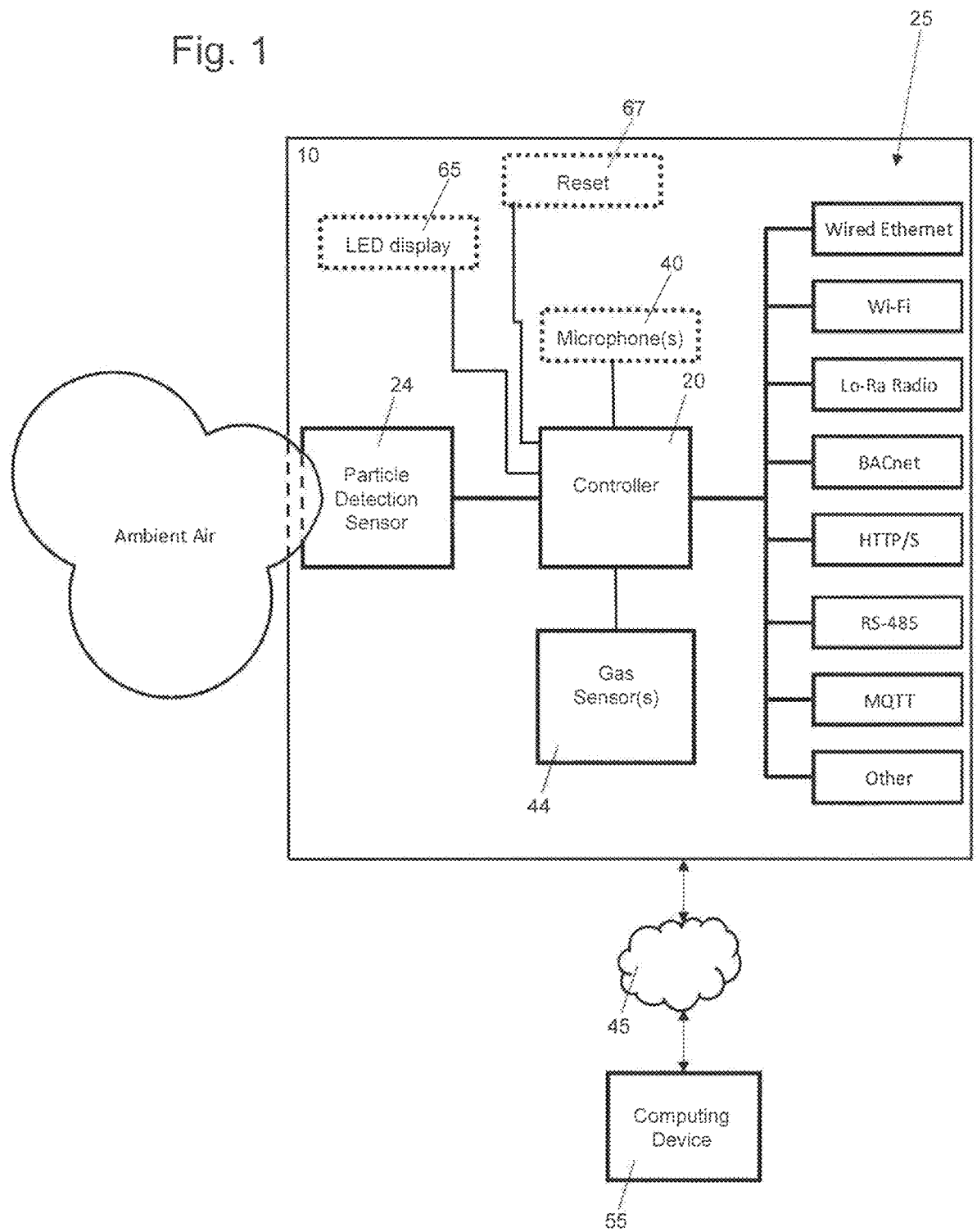
FIG. 1 is a schematic diagram illustrating a sensor device and system in accordance with embodiments of the present disclosure.

The presently disclosed subject matter now will be described more fully hereinafter with reference to the accompanying drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims.

It will be appreciated that reference to "a", "an" or other indefinite article in the present disclosure encompasses one or more than one of the described element. Thus, for example, reference to a sensor may encompass one or more sensors, reference to a histogram may encompass one or more histograms and so forth.

As shown in FIGS. 1 through 4, in various embodiments, a sensor device 10 can comprise hardware and firmware elements, including an electronic controller 20, a particle detection sensor 24 and one or more additional sensors such as gas sensor(s) 44. The device 10 can be formed with access ports (e.g., a network connector, a USB port, etc.) to enable connection with various internal components of the controller 20. In various embodiments, an interface wiring pluggable terminal block can be secured to the device 10. Various optional transmission protocols and wiring schemes are exemplified at 25 for facilitating connections among internal and external elements as described herein. These connections can be implemented through wireless protocols such as Bluetooth, Wi-Fi, Z-Wave, LoRa, NFC, and any other standardized or ad-hoc wireless (radio) protocol. Further, these connections can be implemented through fiber, infrared, or ultra-sonic communication protocols, for example.

The controller 20 can act as a computing device and can include a main computing board (not shown) with a microcontroller or mini-computing device such as a Raspberry Pi™, for example. The particle detection sensor 24 can be secured within, outside or to the sensor device 10 and is in communication with the controller 20. A Power over Ethernet (PoE) regulator, a relay circuit connector and various interface relays can be secured to the main computing board. The interface relays link the mini-computing device to one or more sensor components on the board, for example. An analog to digital (A to D) converter can also be secured to the main computing board. It will be appreciated that various embodiments of the present disclosure operate as an aspirating sensor device whereby air is drawn through one or more pipes and the particle detection sensor 24 and an ingestion fan are positioned remotely from the piped air input for operation in distributed and not collocated form accordance with the description herein.

Figure 2:
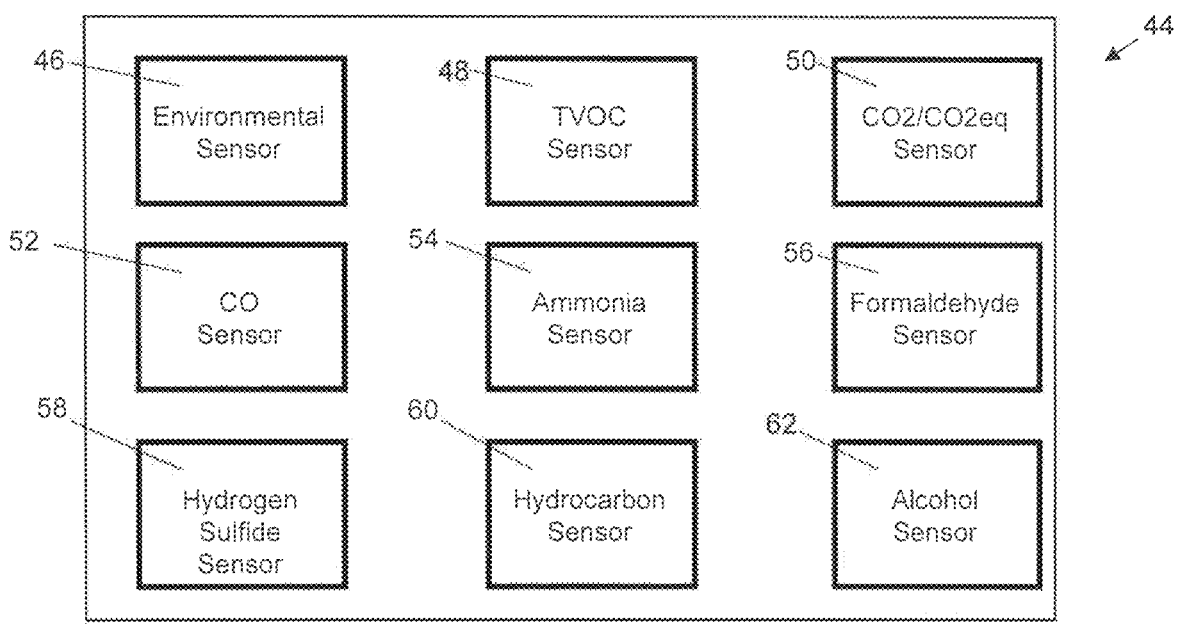
FIG. 2 is a schematic diagram illustrating a gas sensor device in accordance with embodiments of the present disclosure.

As shown in FIG. 2, in various embodiments, the gas sensor(s) 44 can include an environmental sensor 46, a total volatile organic compound (TVOC) sensor 48, a carbon dioxide and/or carbon dioxide equivalent sensor 50, a carbon monoxide sensor 52, an ammonia (NH3) sensor 54, a formaldehyde sensor 56, a hydrogen sulfide sensor 58, a hydrocarbon sensor 60, which may sense gases such as methane, propane, pentane and alkenes, for example, and an alcohol sensor 62. In various embodiments, the environmental sensor 46 is a temperature, humidity and barometric pressure sensor which may incorporate 16-bit A to D conversion for resolution of very small changes in local air pressure. This capability allows for detection of anomalies in air conditioning operation, open windows and open doors, for example. It will be appreciated that gas sensor 44 can be a single sensor with capabilities to sense gases such as described above or may be multiple sensors with such capabilities. The gas sensor(s) 44 can be maintained within or secured to the sensor device 10 and the gas sensor(s) 44 is not required in all aspects of the present disclosure.

In various embodiments as noted elsewhere herein, the environmental sensor 46 includes an air pressure sensor to detect air pressure levels. Such detection can assist in implementations within certain environments (e.g., hospitals and other healthcare facilities) where certain levels of air pressures may be mandated. In various embodiments, the sensor device 10 described herein can be augmented with artificial intelligence, such as voice-activated query and response functionality to enable a user onsite to configure and/or query a device for feedback.

In various embodiments, many types of gases, aerosols (suspensions) and evaporative products can be sensed by gas sensor 44 and classified through use of multi-channel gas sensing. Gases are sensed by interaction with specialized metal oxide layers micro-machined onto ceramic substrates which are heated to a specific temperature. These sensors are available as commercial integrated circuits interfaced with the microcontroller using analog and I2C protocols. Each sensor provides separate measurements of several general types of gases. These types include, but are not limited to, reducing gases, oxidizing gases, ammonia containing gases, carbon dioxide equivalent, and volatile organic compounds (VOCs). This array of chemistries is sufficient to capture the profile of most commercial products that outgas and most naturally occurring gases including combustion gases.

It will be appreciated that such sensors can suffer the challenge of cross gas response, where a given sensor responds primarily to one type of gas but to a lesser degree to other unintended gases. In various embodiment, programming executable by the processor of the controller 20 functions to resolve these cross responses and provide the best possible indications for specific gases and substances.

As further shown in FIG. 1, the sensor device 10 may optionally include one or more microphones 40 maintained therein or secured thereto as shown in dashed lines, for use in embodiments where sound detected from the microphone (s) may assist with identifying a source or location of a pollutant, for example. I2S is an electrical serial bus interface standard used for connecting digital audio devices, and this can be used in connecting microphones 40 to the controller 20, for example. Further optional elements that can be incorporated with the sensor device 10 include a speaker, an LED display 65 for red, green, blue and mixed color alerting, a system reset button 67 and other elements. The alerting LED 65 can communicate with the controller 20 and can be maintained within or secured to the sensor device 10. In various embodiments, alerting LED 65 can be exposed on the surface of the sensor device 10 and use full color and intensity control to display various system status and alerting indications. This alerting LED 65 may also be completely disabled for application where "hidden" operation is desirable. Further, the sensor device 10 can include two electrically isolated relays that may be used to connect a standalone unit to a siren/strobe, a conventional alarm panel, or any other low voltage circuit. In various embodiments, two relays are provided, and these may be associated with any two thresholds or rules created in the firmware. It will be appreciated that wired electrical bus connections may include CANBUS, MODBUS, RS-485, and others for wired connections to outside data sources and for direct signaling to external related systems such as HVAC controls, building management and automation systems and others.

A driver function extracts information from the sensor device 10 and makes that information available to other processes. The driver serves to isolate information consuming processes from any knowledge of the physical or logistical details of the sensor device 10. The driver can obtain information from the sensor device 10 by polling it on a regular basis and maintaining the latest measurement values and/or monitoring data in accessible memory buffers. The polling rate can be determined by a supplied configuration value, for example. The sensor device 10 can also include programmable internal thresholds that generate active triggers when limit values are crossed. These triggers can be communicated to the processor using interrupts, enabling much faster and more deterministic reaction to events than is possible using polling.

The particle detection sensor 24 can communicate with the controller 20 via serial interface, for example, and a PoE regulator, battery or other power source can be provided for power. The analog signal from microphone(s) 40 can be converted using an AD converter which communicates with the controller 20. The controller 20 can further include a memory storing programming for execution by a processor, and an application programming interface (API) and web portal to facilitate communications with external systems (e.g., computing device 55) and programs.

The particle detection sensor 24 can be a universal particle concentration sensor, for example, which can be used to determine the number of suspended particles in the air and the concentration of particles in the air and output them in the form of a digital interface, as described elsewhere herein. This sensor measures the concentration of suspended particles in the air to provide correct concentration data over time. It will be appreciated that the scattering principle can be used in this sensor, i.e., it produces scattering by utilizing structured light to irradiate suspending particles in the air, then collects scattering light at a specific angle, and finally obtain the curve of scatted light changes over time. Equivalent particle diameter and the number of particles with different diameter per unit volume can be calculated by the microprocessor by using, for example, MIE theory.

In various embodiments, the particle detection sensor 24 can be a laser reflection particle detection sensor, and can include an ingestion fan, wherein the ingestion fan is secured within the device 10 so as to induce air flow across the particle detection sensor 24 in a way that facilitates accurate and effective readings. The particle detection sensor can detect the presence of pollutants such as smoke and vaping, for example. In various embodiments, the output of the particle detection sensor 24 is provided as the quality and number of each particles in size bins with each of two or more different sizes per unit volume, where the unit volume of particle number is 0.1 L and the unit of mass concentration is $\mu g/m^3$. The output results can be binned into multiple categories. For example: 0.3~1.0 uM, 1.0~2.5 uM, and 2.5~10 uM. Based upon the types of particulates to be detected, a particle detection sensor 50 with the ability to detect only one particulate size can be used. For example, 2.5 uM particles are characterized as more dangerous to humans then 10 uM particles at the same density. Thus, in various embodiments, a sensor may be set to detect particulates of size 2.5 uM. It will be appreciated that other types of particle detection sensors beyond laser reflection particle detection sensors can be employed according to the present disclosure, including but not limited to ultrasonic and ionization particle detection sensors.

Embodiments of the controller firmware (operating program) of the device 10 can perform several tasks required to implement the intended functions described herein, including file system operations, storage of configuration values, polling all sensors for current data, controlling output devices, web page hosting, API implementation (e.g., MQTT and specific to remote systems), security and login accounts, visual (e.g., JPG, MJPEG, H264 or other video compression technologies) dashboard generation and streaming, processing current sensor data to isolate desired responses, testing responses against thresholds and schedules to develop detected event notifications, generation and delivery of detected event notifications to external devices, and delivery of current data and detected event notifications through API and a visual dashboard as described elsewhere herein.

As described above, the sensor device 10 can include multiple hardware devices such as particle detection sensor 24 and gas sensor(s) 44 that measure physical environmental conditions. These sensors can be polled by the controller 20 to retrieve monitoring data such as current measurement values, for example. The sensor polling operations can include a mixture of direct wired binary logic connections between the controller and peripherals (sensors, LEDs, relays) and serial data communications with specific sensors that are configured for these serial modes. For example, the particle detection sensor 24 can communicate with the controller 20 using the standard asynchronous serial protocol and UART commonly used by RS-232 implementations but at the internal logic levels of 3.3V as appropriate for the controller 20. Output relays can be controlled by direct logic level wired connections to the controller 20.

Figure 3:
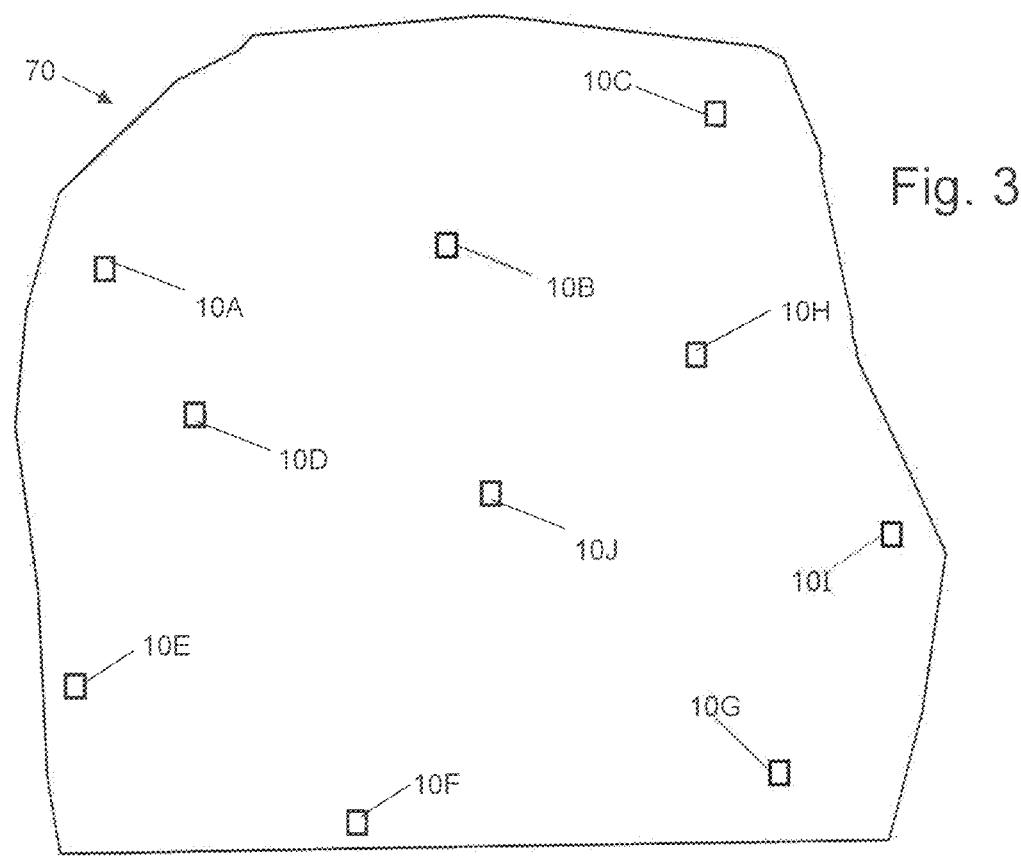
FIG. 3 is a diagram illustrating an environment with a plurality of sensor devices deployed in accordance with embodiments of the present disclosure.

It will be appreciated that a single sensor device 10 can be employed in an environment or multiple sensor devices 10 can be employed in accordance with the present disclosure. FIG. 3 illustrates an environment 70 with multiple sensor devices 10A-10J dispersed throughout.

Figure 4:
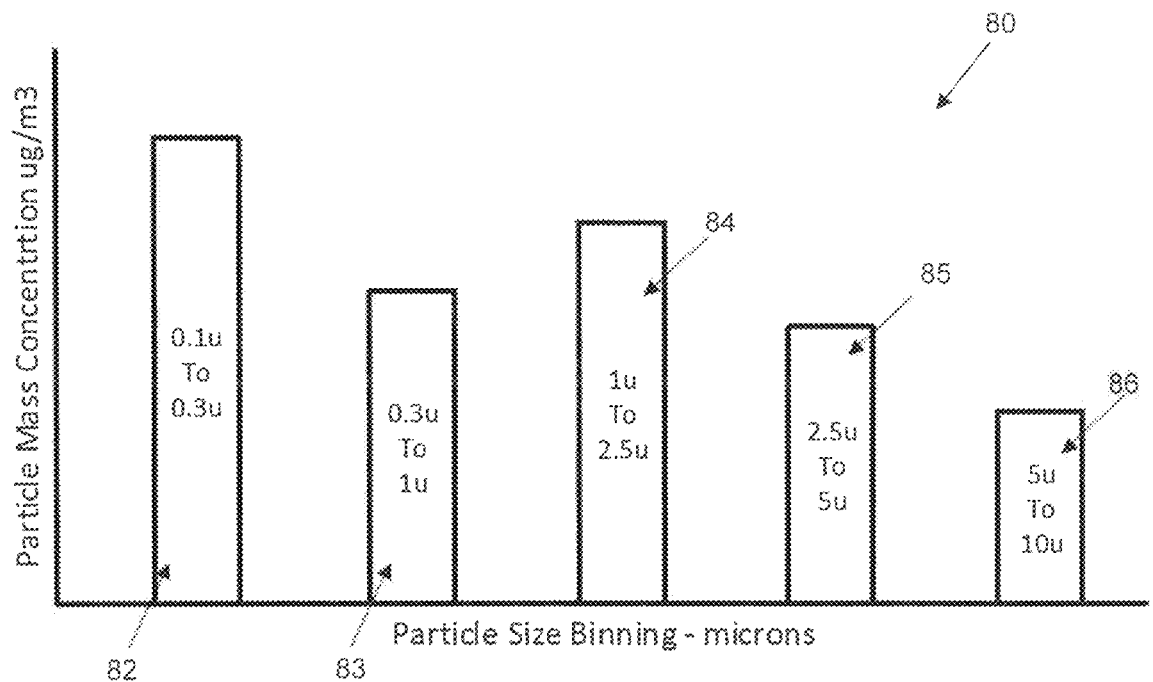
FIGS. 4 through 8 are illustrative histograms in accordance with embodiments of the present disclosure.

FIG. 4 shows an exemplary particle mass concentration histogram 80 representing a measured collection of particles from a given particle detection sensor (e.g., 24 in FIG. 1) in accordance with embodiments of the present disclosure. The sample histogram 80 represents the ambient environment being evaluated and shows an array of particle measurement values in each of the bins. In histogram 80, the particle binning sizes are shown on the x-axis, including a particle bin 82 for particles of sizes ranging from 0.1 micron to 0.3 microns, a particle bin 83 for particles of sizes ranging from 0.3 microns to one micron, a particle bin 84 for particles of sizes ranging from 1 micron to 2.5 microns, a particle bin 85 for particles of sizes ranging from 2.5 microns to five microns, and a particle bin 86 for particles of sizes ranging from five microns to ten microns. The particle mass concentration is on the y-axis and is measured in micrograms/cubic meter. It will be appreciated for purposes of the present disclosure that use of the term "size" can encompass a specific size particle (e.g., 1 micron) or a range of sizes of particles (e.g., 1-2.5 microns). As can be seen in FIG. 4, the monitoring data collected from a given particle sensor shows a greater mass concentration of particles in the bin 82 for the smallest size particles than in any other bin, and further shows the lowest mass concentration of particles in the bin 86 for the largest size particles.

Figure 5:
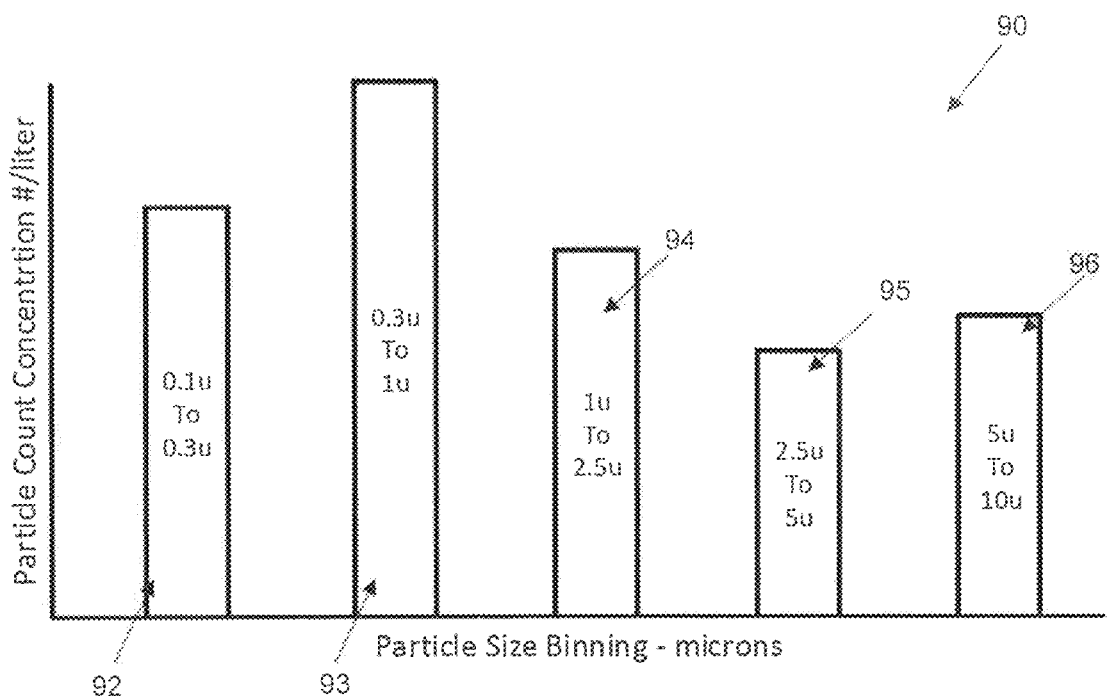

FIG. 5 shows an exemplary particle count histogram 90 representing a measured collection of particles from a given particle detection sensor in accordance with embodiments of the present disclosure. The sample histogram 90 represents the ambient environment being evaluated and shows an array of particle measurement values in each of the bins. Whereas histogram 80 in FIG. 4 shows particle mass concentration values as the particle measurement values, histogram 90 shows particle count values as the particle measurement values. In histogram 90, the particle binning sizes are shown on the x-axis, including a particle bin 92 for particles of sizes ranging from 0.1 micron to 0.3 microns, a particle bin 93 for particles of sizes ranging from 0.3 microns to one micron, a particle bin 94 for particles of sizes ranging from 1 micron to 2.5 microns, a particle bin 95 for particles of sizes ranging from 2.5 microns to five microns, and a particle bin 96 for particles of sizes ranging from five microns to ten microns. The particle count is on the y-axis and is measured in the number of particles per liter. As can be seen in FIG. 5, the monitoring data collected from a given particle sensor shows a greater particle count in bin 93 than in any other bin.

Figure 6:
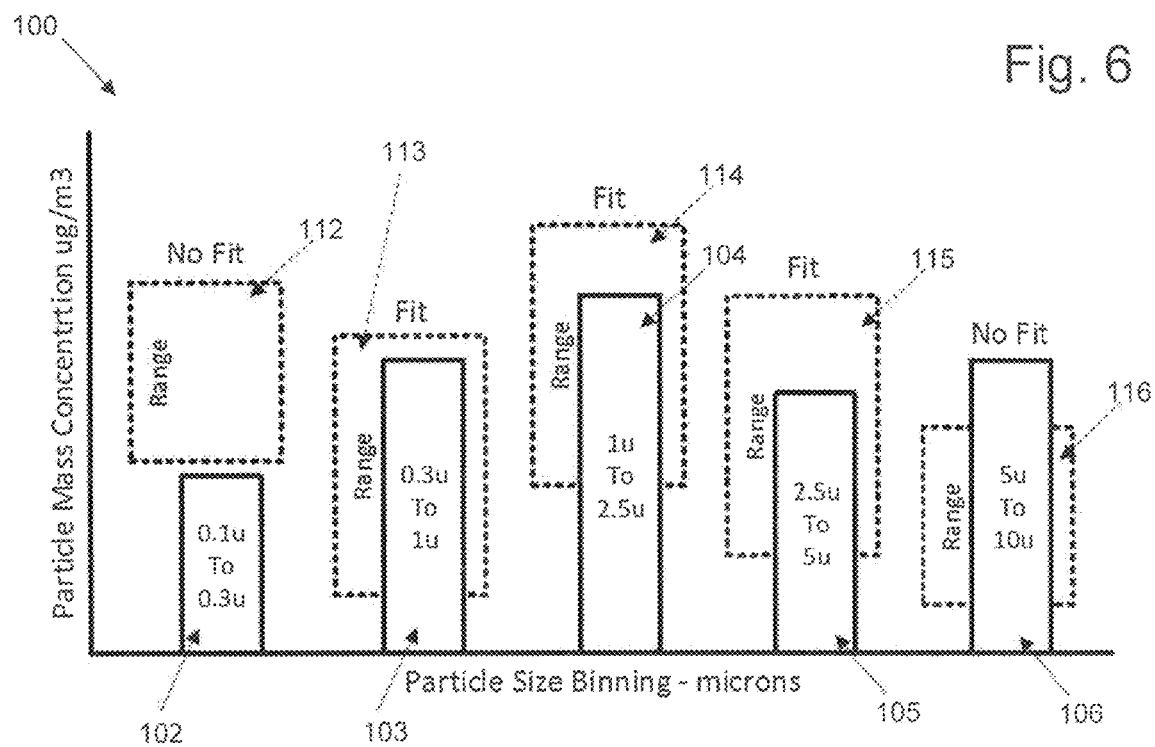

FIG. 6 shows an exemplary particle mass concentration histogram 100 representing a sample of measured particles from a given particle detection sensor (in solid lines) in accordance with embodiments of the present disclosure. In histogram 100, the particle binning sizes are shown on the x-axis, including a particle bin 102 for particles of sizes ranging from 0.1 micron to 0.3 microns, a particle bin 103 for particles of sizes ranging from 0.3 microns to one micron, a particle bin 104 for particles of sizes ranging from 1 micron to 2.5 microns, a particle bin 105 for particles of sizes ranging from 2.5 microns to five microns, and a particle bin 106 for particles of sizes ranging from five microns to ten microns. The particle mass concentration is on the y-axis and is measured in micrograms/cubic meter. As can be seen in FIG. 6, the measured collection of particles is overlaid on an exemplary vape range profile histogram (shown in dashed lines). The vape range profile histogram represents a range of measurements for particles of each size range associated with each bin 102-106 and the vape range profile histogram is represented by rectangles in dashed lines. As can be seen in FIG. 6, the vape range profile histogram specifies particle measurement values within the various particle size bins. It will be appreciated that particle measurement values can encompass a single value or a range of values. In FIG. 6, the vape range profile histogram for particles from 0.1 micron to 0.3 micron in bin 102 is shown as a range that is above the actual measured collection of particles in bin 102 of the given particle detection sensor. In various embodiments, the range of high and low particle measurement values correspond to the presence or absence of a pollutant to be detected in the environment. It will be appreciated that profile histograms for a variety of pollutants can be defined and stored in a computer memory as described elsewhere herein.

In various embodiments, a profile histogram for a pollutant (e.g., vape) can have particle measurement values for each bin that can be represented as exclusionary or inclusionary. In other words, the range can be considered inclusionary if it is necessary for the measured particles for a given bin to fall at least partially within the defined range in order to be a possible match for the pollutant (e.g., vape) being detected. Further, the range can be considered exclusionary if it is necessary for the measured particles for a given bin to fall outside of the defined range in order to be a possible match for the pollutant (e.g., vape) being detected.

The vape ranges in the profile histogram of FIG. 6 are inclusionary. As can be seen, the vape range 112 for the first bin 102 is not met by the measured particles in the first bin. Thus, the first bin is a "no fit" measurement with the measured particles in this bin 102 having a mass concentration measurement outside of the vape range 112. The vape range 113 for the second bin 103 is a "fit" measurement since the measured particles fall within this vape range 113 at least for the high end of the measured particle mass concentration in this bin 103. In other words, the highest particle mass concentration in bin 103 is lower than the high end of the vape range 113. This is an indication of a possible match for vaping as detected from the sensor device 10 employed in the measurements according to embodiments of the present disclosure. Bin 104 also shows a fit with vape range 114 and bin 105 shows a fit with vape range 115 for the high end of the measured particle mass concentration in these bins 104, 105. However, bin 106 shows a no-fit with vape range 116 as the low measurement of particle mass concentration in bin 106 is below the bottom of vape range 116, and the high measurement of particle mass concentration in bin 106 is above the top of vape range 116.

It will be appreciated that determining whether measured particles for a given bin are a "fit" or "match" for a given profile histogram can be based upon whether the highest particle measurement value in a given bin is lower than the high end of a range of values for the given bin in a profile histogram for the pollutant being measured, regardless of whether the lowest particle measurement value in the given bin is lower, the same or higher than the low end of the range of values in the profile histogram. This can be seen with bin 103 in FIG. 6. It will further be appreciated that embodiments of the present disclosure can require that the lowest particle measurement value in a given bin be the same or higher than the low end of the range of values in the profile histogram in order to be considered a fit or match. It will further be appreciated that embodiments of the present disclosure can require that the lowest particle measurement value in a given bin be the same or higher than the low end of the range of values in the profile histogram for the given bin and further that the highest particle measurement value in the given bin be the same or lower than the high end of the range of values in the profile histogram for the given bin in order to be considered a fit or match.

In the embodiment according to FIG. 6, three out of five bins indicate a possible match for the measured pollutant, which is vape in this case. In various embodiments, this sixty percent degree of fit can be compared with a threshold degree of fit in order to conclude whether or not the sample histogram represents a pollutant signature. This approach can be applied to sample values of particle counts (e.g., FIG. 5) in similar fashion.

According to various embodiments, a match quality value is determined based on comparing a sample histogram of actual measured particle values with a profile histogram for a given pollutant, such as illustrated in FIG. 6. The match quality value is determined in order to evaluate whether a detected event notification is issued indicating the presence of the given pollutant in a given environment where one or more sensors 10 are deployed. In some embodiments, the match quality value is determined based on whether a sample particle measurement value fits between a value range in the profile histogram for one of the bins. The match quality value can further be determined based on whether the multiple particle measurement values for multiple respective bins fit between a value range in the profile histogram for one or more of the multiple respective bins. In further embodiments, the match quality value is determined based on the degree to which a sample particle measurement value for a given bin fits between a value range in the profile histogram for the given bin. Further, the match quality value may be determined based on the degree to which multiple particle measurement values for multiple respective bins fit between a value range in the profile histogram for one or more of the multiple respective bins. In still further embodiments, the match quality value can be determined, at least in part, based on whether one or more particle measurement values for one or more respective bins do not fit between a value range in the profile histogram for the one or more bins. It will be appreciated that still other embodiments can determine a match quality value in other ways, such as by measuring the aggregated value differences between measured sample values and a profile value for each bin (see discussion of FIG. 9 elsewhere herein) or for groups of bins including small, medium and large bins.

Figure 7:
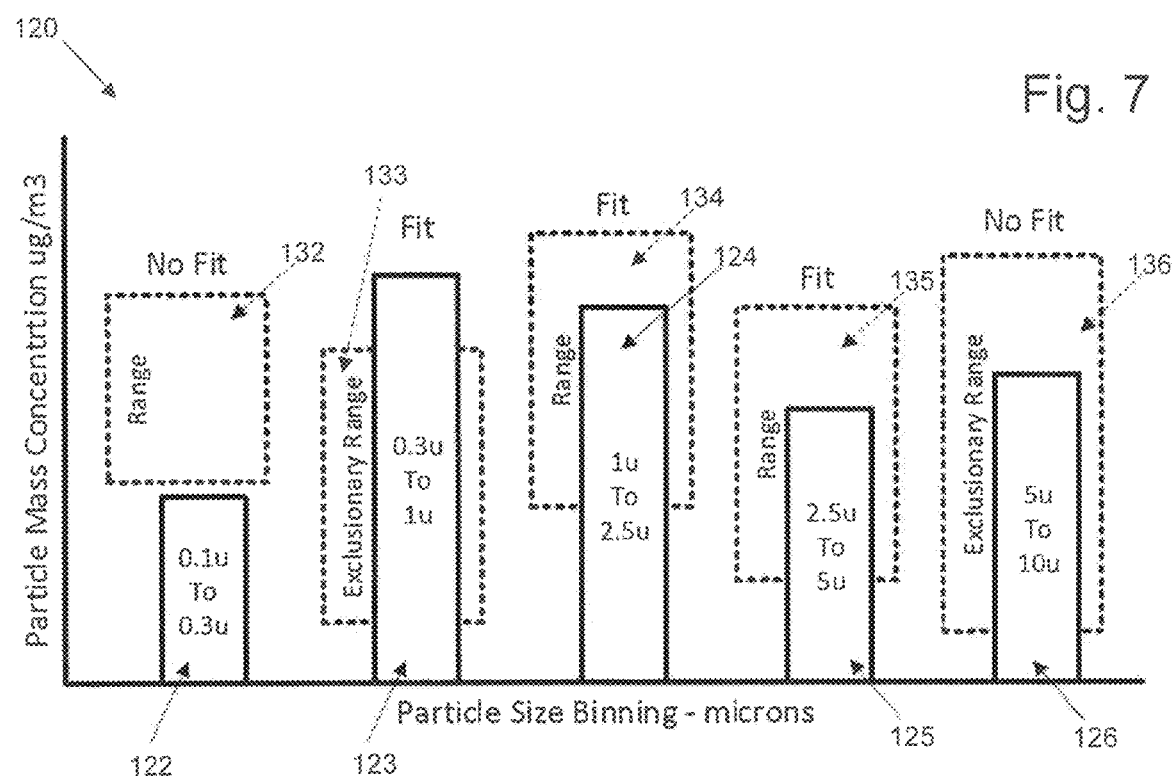

FIG. 7 shows an exemplary particle mass concentration histogram 120 representing a measured collection of particles from a given particle detection sensor in solid lines and a comparison with a profile histogram in dashed lines in accordance with embodiments of the present disclosure. In histogram 120, the particle binning sizes are shown on the x-axis, including a particle bin 122 for particles of sizes ranging from 0.1 micron to 0.3 microns, a particle bin 123 for particles of sizes ranging from 0.3 microns to one micron, a particle bin 124 for particles of sizes ranging from 1 micron to 2.5 microns, a particle bin 125 for particles of sizes ranging from 2.5 microns to five microns, and a particle bin 126 for particles of sizes ranging from five microns to ten microns. The particle mass concentration is on the y-axis and is measured in micrograms/cubic meter. FIG. 7 further shows histogram 100 overlaid on an exemplary vape range profile histogram. The vape range profile histogram represents a range of measurements for particles of each size range associated with each bin 122-126 and the vape range profile histogram is represented by rectangles in dashed lines. As can be seen in FIG. 7, vape ranges 133 and 136 are exclusionary ranges. As can further be seen in FIG. 7, the measurement in bin 122 is a "no fit" with vape range 132, the measurement in bin 123 is a "fit" with vape range 133, the measurement in bin 124 is a "fit" with vape range 134, the measurement in bin 125 is a "fit" with vape range 135, and the measurement in bin 126 is a "no fit" with vape range 136.

In FIG. 7, there are thus three out of five bins that indicate a possible match for the measured pollutant, which is vape in this case. In various embodiments, this sixty percent degree of fit can be considered a match quality value and this value can be compared with a threshold degree of fit in order to conclude whether or not the sample histogram represents a vape signature. This approach can be applied to sample values of particle counts (e.g., FIG. 5) in similar fashion.

Figure 8:
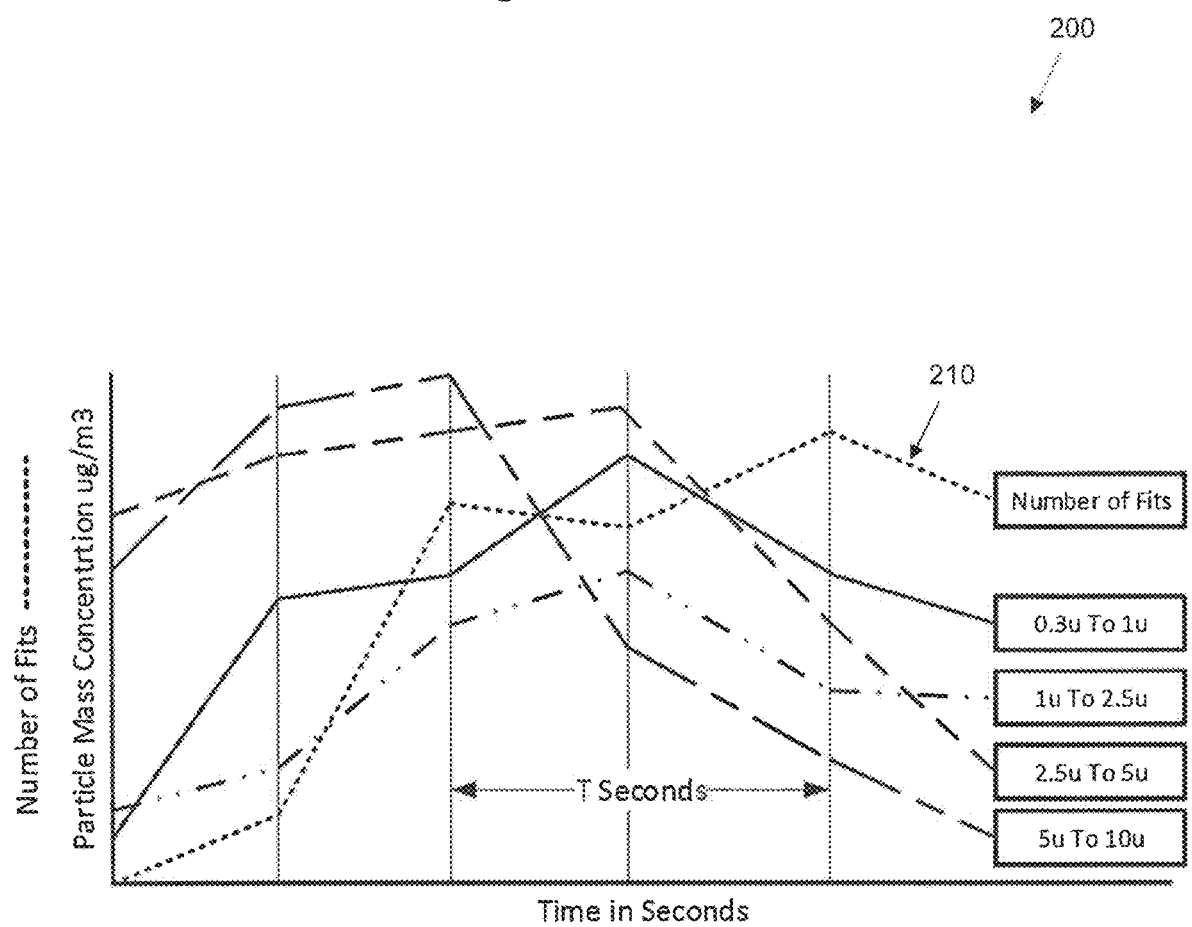

FIG. 8 is a graph 200 depicting the values of a time series of particle mass concentration sample histograms. For example, a first sample histogram may be developed for a given sensor device 10 at time T=0, a second sample histogram may be developed at time T=1 and so forth. Each histogram in the time series can have a range matching operation performed as described above in connection with FIGS. 6 and 7. The number of fits can be plotted over the time series as described above and as indicated at 210 in FIG. 8. The fit number plot 210 can be evaluated and the match quality value can be determined according to whether the number of fits is above a specific numeric threshold for at least a certain time (e.g., T seconds in FIG. 8) indicating a pollutant (e.g., vape) detection. Additionally, the difference in the attack and decay times of the small and large particles can be used to determine the distance from the source of the particles. For example, the velocity of the particles is dependent on size so at any distance from the source of the pollutant there will be a "wave" of the pollutant that will increase in concentration, then will fall-off over time. The rise time and fall time of the wave of pollutant will depend on the local environment, and the different particle sizes will have different rise and fall times within the overall pollutant wave itself. These techniques can be applied to sample values of particle counts in the same fashion as to particle mass concentration sample values.

In various embodiments, particle measurement values used in multiple sample histograms are measured at a plurality of intervals over a time span. The match quality value can be determined based on the highest degree to which a particle measurement value as measured at the plurality of intervals fits between a value range in the profile histogram for a given bin. In some embodiments, the match quality value can be determined based on the highest degree to which multiple particle measurement values for multiple respective bins fit between respective value ranges in a profile histogram for the multiple respective bins. According to various embodiments, the match quality value can further be determined based on the average degree to which a particle measurement value as measured at the plurality of intervals fits between a value range in the profile histogram for a given bin. In still other embodiments, the match quality value can be determined based on the average degree to which multiple particle measurement values for multiple respective bins fit between respective value ranges in a profile histogram for the multiple respective bins.

Figure 9:
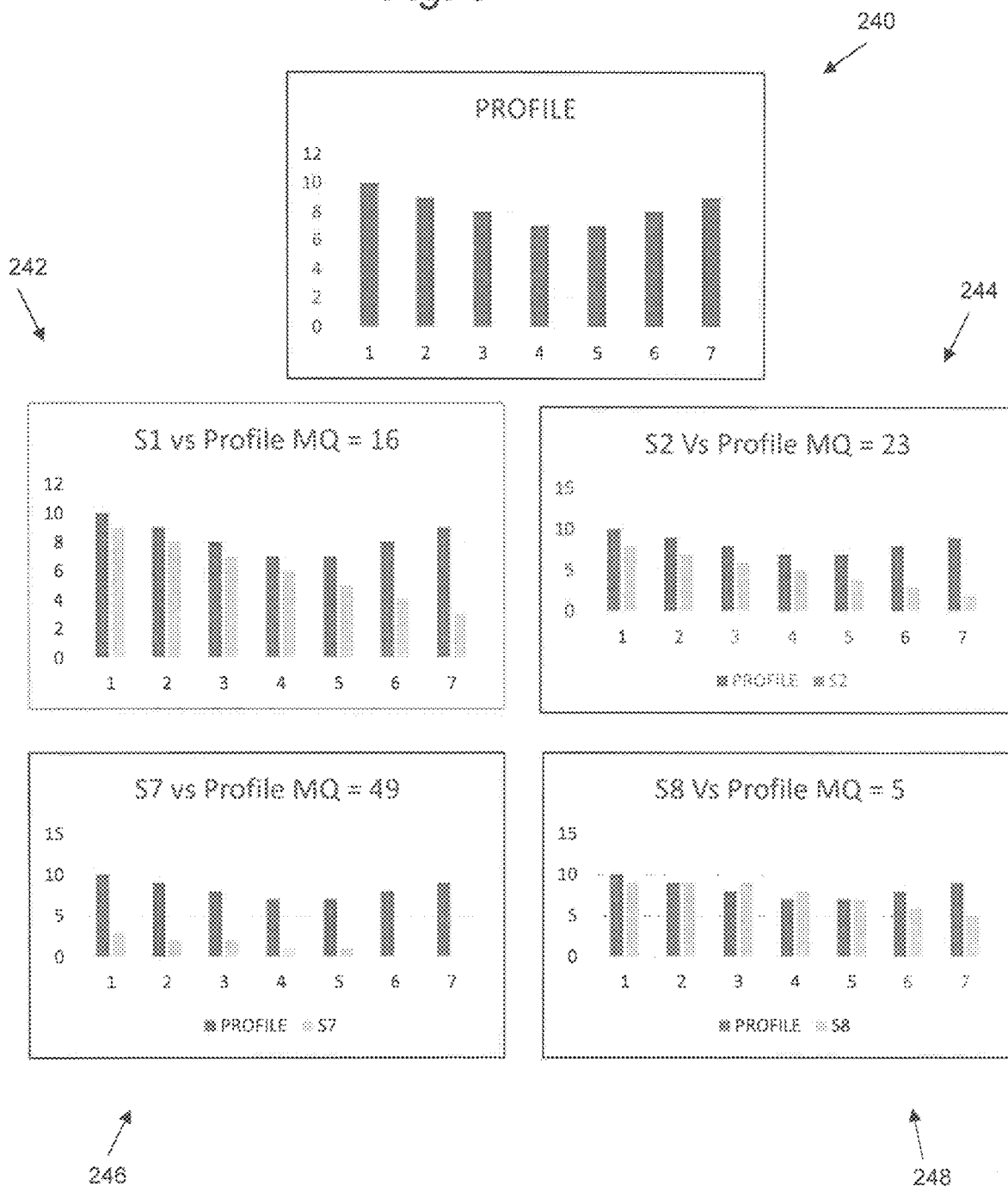
FIG. 9 shows an exemplary profile histogram and multiple sample histograms in accordance with embodiments of the present disclosure.

As shown in FIGS. 9 and 10, match quality values for a series of sensors deployed in an environment are shown. In FIG. 9, a profile histogram is shown at 240 and comparison of sample histograms to the profile histogram 24 are shown at 242, 244, 246, 248 for each of sensors S1, S2, S7 and S8, respectively. The sample histograms for the multiple sensors can be considered a series of histograms. As can be seen in FIG. 9, sensor S1 has a histogram 242 with a match quality value of 16, sensor S2 has a histogram 244 with a match quality value of 23, sensor S7 has a histogram 246 with a match quality value of 49 and sensor S8 has a histogram 248 with a match quality value of 5 since the aggregated difference between the measured sample value and the profile value across all seven bins of sensor S8 totals five. As shown in FIG. 10, the match quality values are determined for each sensor S1-S20 by measuring the aggregated value differences between measured sample values and the profile value for each of seven bins, with lower match quality values indicating a closer match in this embodiment. In various embodiments, a high measurement of particles in the largest size bin in a short time frame, followed by a fairly rapid drop in larger particle measurements thereafter for the same sensor are indicative of vape detection and close proximity of the given sensor to the source of the vaping activity. For example, in a situation where a person such as an employee in a cubicle in an open office setting is vaping to obtain a quick hit of nicotine surreptitiously, even a single exhalation would result in a histogram where the larger particles would decline quickly. In some embodiments, a first vape profile histogram is established for an early time frame followed by a second vape profile histogram for a later time frame, and in instances where there is a high match quality for both profile histograms, a detected event notification is issued.

Figure 11:
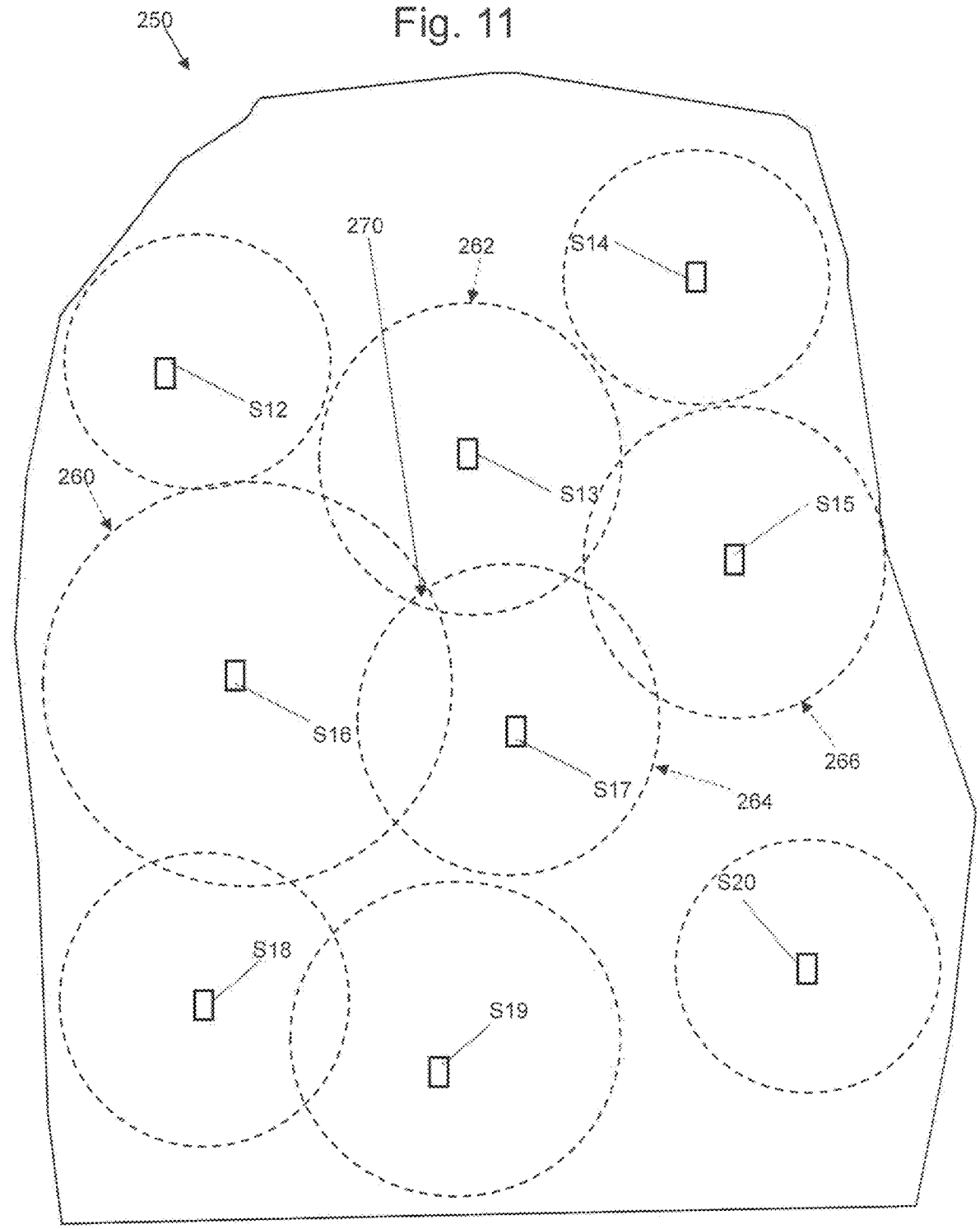
FIG. 11 is a diagram illustrating an environment with a plurality of sensor devices and exemplary match quality value representations in accordance with embodiments of the present disclosure.

According to aspects of the present disclosure, a distance of a source of a pollutant from one or more sensor devices as described herein can be determined based upon the particle measurement values at a given time or over a given time span. In FIG. 11, for example, the location of sensors S12-S20 within environment 250 are shown along with representative match quality values from FIG. 10. The match quality values can be represented graphically as circular or oval shapes, for example, with the size of the shape dependent upon the match quality value and overlapping areas deemed to indicate a greater potential for being a source of a pollutant. In some embodiments, the size of the shape surrounding a sensor with the best match quality value may be smaller and/or color coded to indicate a higher possibility of including the source of the pollutant. In other embodiments, the size of the shape surrounding a sensor with the best match quality value may be larger and/or color coded to potentially overlap with other shapes corresponding to other sensors as an approach to triangulate or otherwise use overlapping match quality value shapes to identify a potential source of a pollutant. For example, in FIG. 10, the match quality value of sensor S16 is shown as dashed shape 260, the match quality value of sensor S13 is shown as dashed shape 262, the match quality value of sensor S17 is shown as dashed shape 264 and the match quality value of sensor S15 is shown as dashed shape 266. In such an example, embodiments of the present disclosure may determine that the area of overlap 270 is a highly likely location of the source of a detected pollutant and suitable event notifications may be generated as a result. The distance of the pollutant source from the sensor may be determined based on the represented size of the shape surrounding the sensor on a user interface and the overlap area(s) indicating a possible source. For example, if the size of the shape surrounding sensor S16 represents a twenty-foot radius and the overlap area 270 is approximately seventy degrees along the circumference (with zero degrees being the top-most or 12 o-clock position), then the source of the pollutant may be located accordingly. In various embodiments, based on the match quality value for each of the sensors in an environment, a relative proximity of each of the sensors to the source of the pollutant is determined. It will be appreciated that the diagram of environment 250 in FIG. 11 may be portrayed on a visual display of a user device (e.g., computing device 55) and changed over time as the environment 250 is monitored for pollutants.

In some embodiments, detecting a potentially likely location of a source of a pollutant may trigger additional sensors such as a microphone or video camera in an effort to further confirm the source and/or record information that may assist with identifying the source and any human perpetrators.

As described elsewhere herein, embodiments of the present disclosure incorporate a gas sensor 44 with the sensor device 10. In such embodiments, measured gas sensor values can be included in the elements of the sample histogram (e.g., histograms 80 and 90 in FIGS. 4 and 5, respectively). Should an evaluation as described herein lead to a detected event notification, such a notification can include a measurement of one or more gases as determined by the gas sensor 44 and communicated to the device 10 such as through controller 20. Further, the array of the sample histogram can show the measurement of the one or more gases as determined by the gas sensor 44. It will be appreciated that there may be a profile histogram where each detected gas is represented in a different column of the histogram and a match quality is determined based on comparing actual measurements obtained for each gas with the gas profile histogram. According to some embodiments, a sample histogram for a gas such as CO may show the highest gas measurements at a time or time period different from the highest particle measurements on a sample histogram for particle measurements. In various embodiments, upon changes in the gas histogram indicating a detected event, embodiments of the present disclosure can trigger actions such as turning on a device fan or other actions. In such embodiments, the device fan may be inactive until such time as the detected event occurs to conserve battery, as the device fan may require more current and the gas sensor(s) can be operated under lower current.

Figure 12:
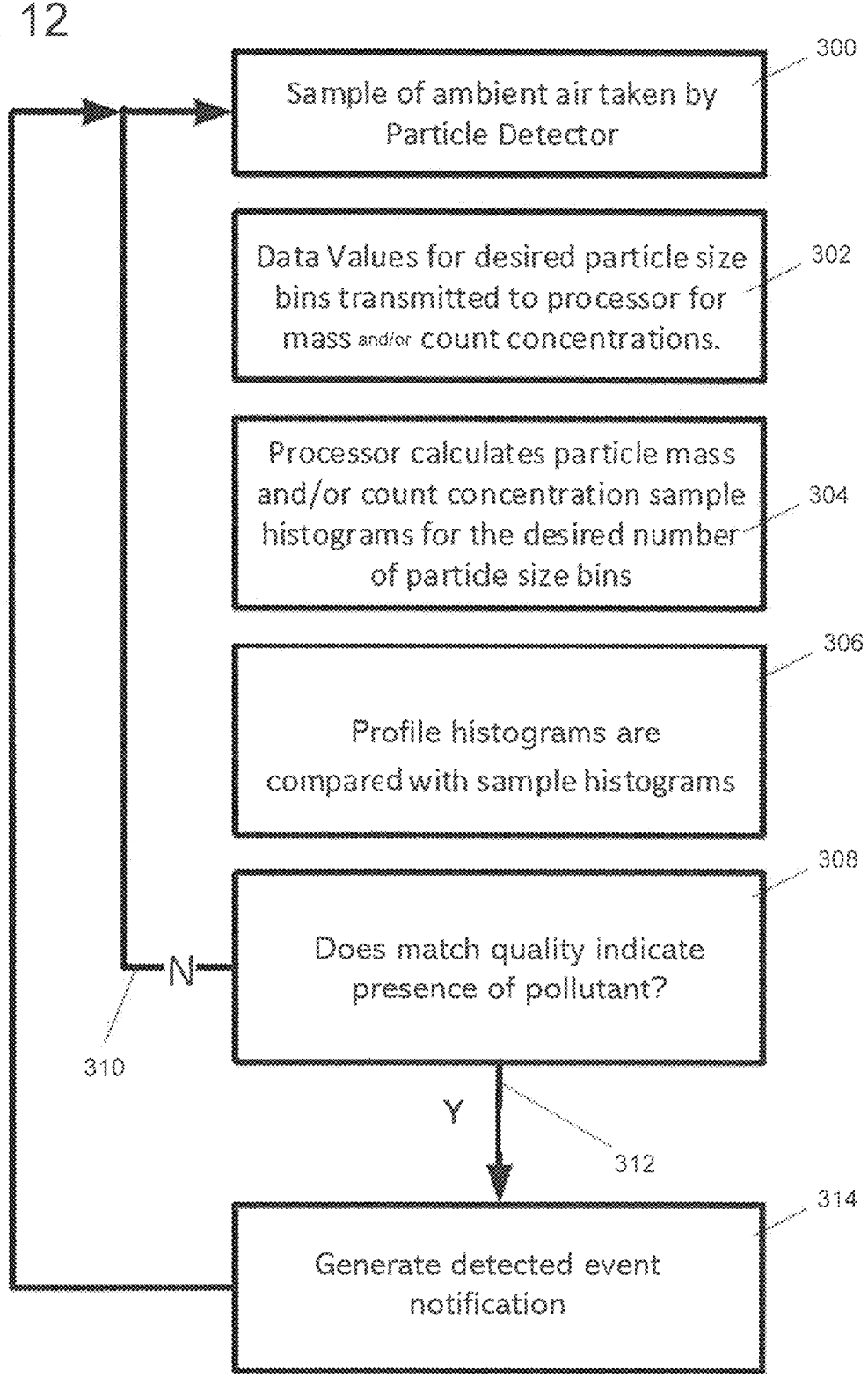
FIGS. 12 and 13 are example flow diagrams illustrating aspects according to embodiments of the present disclosure.
Figure 13:
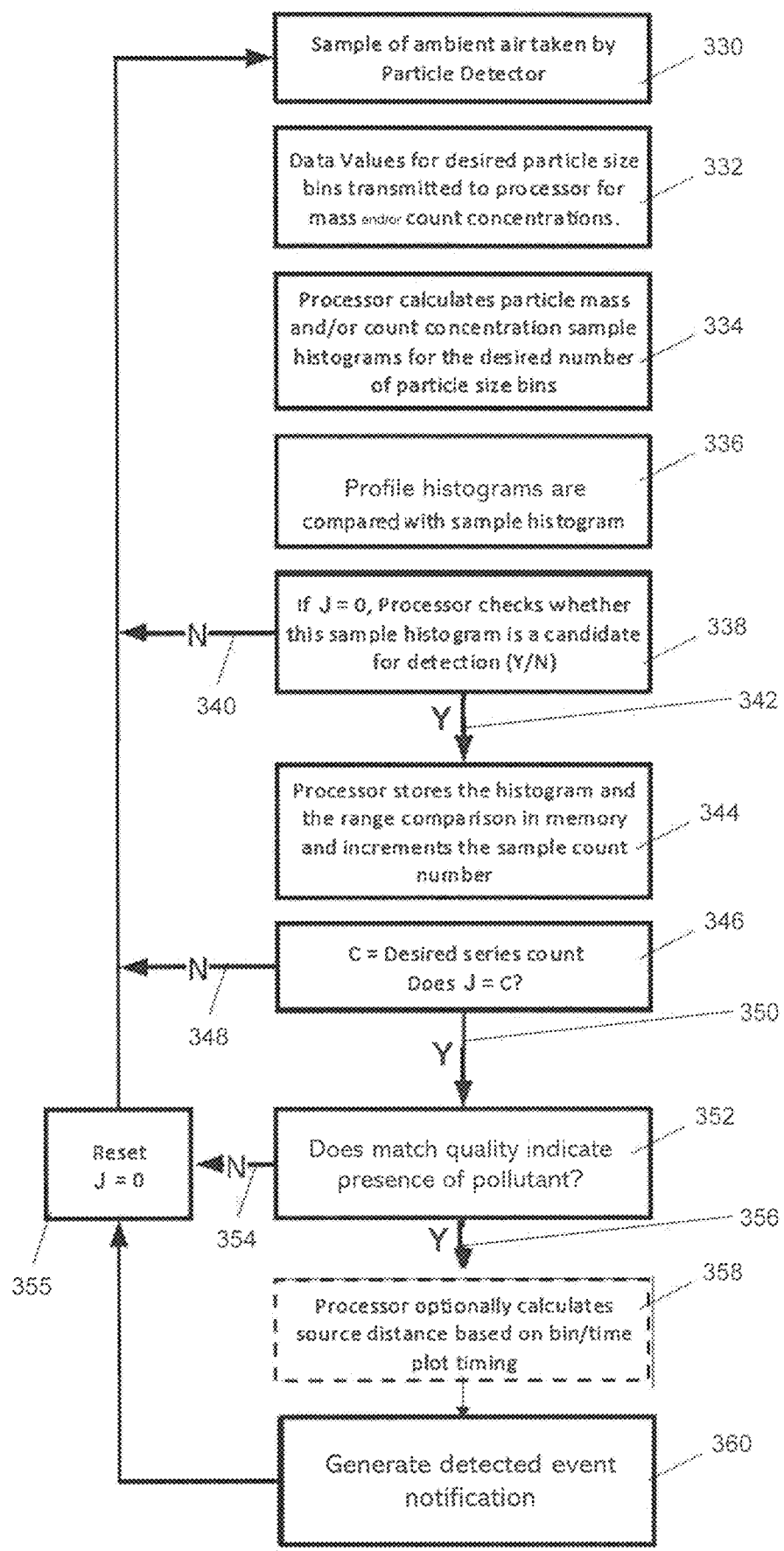

FIGS. 12 and 13 are flow diagrams illustrating processes associated with embodiments of the present disclosure. As at 300 in FIG. 12, a sample of the ambient air is collected by a particle detection sensor 24. As at 302, particle measurement values for each desired particle size bin (see, e.g., FIGS. 4 and 5) are transmitted to the controller 20 for particle mass and/or count concentration determinations. As at 304, the particle mass and/or count concentration determinations are presented as one or more sample histograms for the desired number of particle bins. As at 306, profile histograms are employed and compared with the one or more sample histograms, and as at 308, a match quality determination is made to assess whether a given pollutant is present. If not, as at 310, another sample of ambient air is collected and the process begins again. If so, as at 312, a detected event notification is issued.

In FIG. 13, a sample of the ambient air is collected by a particle detection sensor 24 as at 330. As at 332, particle measurement values for each desired particle size bin are transmitted to the controller 20 for particle mass and/or count concentration determinations. As at 334, the particle mass and/or count concentration determinations are presented as one or more sample histograms for the desired number of particle bins. As at 336, profile histograms are employed and compared with the one or more sample histograms. As at 338, if this is the first collection of particle measurement values (i.e., where sample count variable J equals zero), the controller 20 checks whether the sample histogram is a candidate for detection. if not, as at 340, the sample of ambient air is again collected as at 330. If so, as at 342, the controller stores the sample histogram and the range comparison and further increments sample count variable J by one as at 344. As at 346, if the desired series count C has not been met (i.e., because J is less than C), then as at 348, another sample of ambient air is collected as at 330. As at 350, if the desired series count C has been met (i.e., because J equals C), then as at 352, the match quality is determined and evaluated for whether a pollutant has been detected. If a pollutant has not been detected as at 354, then J is reset to zero as at 355 and another sample of ambient air is collected as at 330. If a pollutant has been detected as at 356, then optionally as illustrated in dashed lines, the controller can determine a distance of the source of the pollutant from one or more sensors as at 358. Whether or not a distance is determined, a detected event notification is generated as at 360 if a pollutant has been detected as at 356.

As described elsewhere herein, in various embodiments, the sensor device 10 can be provided as part of an integrated system including a video monitoring system comprising one or more video cameras adapted to record video of a surveilled environment or premises. The video camera(s) can transmit recorded video and optionally audio to a system such as external computing device or system 55 in accordance with communication methods as will be understood to those of ordinary skill. The sensor device 10 can receive monitoring data from one or more of the group of sensors, which can include the particle detection sensor 24, gas detection sensor(s) 44 and can also generate or employ a profile of one or more detected substances, wherein the profile can be represented as a histogram as described elsewhere herein, for example. When the sensor device determines that at least a portion of the received monitoring data is indicative of an exceeded threshold and/or when the received monitoring data matches that of a generated profile, a communication such as a detected event notification can be transmitted to the external system 55. In the case where the external system 55 is a video monitoring system, the video monitoring system can then initiate video recording of the premises where the sensor device 10 is located. It will be appreciated that the computing device or system 55 can also be an alarm system or a remote management system, for example, and that the instance of computing device 55 in FIG. 1 can represent multiple different devices and/or systems. It will further be appreciated as described elsewhere herein that the particle detection sensor 24 can be maintained remotely from the controller 20 and further that the sensor device 10 can be maintained remotely from computing device 55 in various embodiments.

According to various embodiments and with reference to FIG. 1, the computing device 55 is a communications device such as a desktop computer, laptop, notebook, mobile device, personal communications device such as a smartphone or other computing device and can communicate via network 45 with various devices and systems, including to configure and/or monitor the sensor device 10. In various embodiments, the controller 20 runs an operating system such as Debian Linux, Windows, Android, iOS or other operating system together with dedicated applications. The controller 20 of the sensor device 10 is provided with sufficient physical input/output (I/O), a memory and processing power for real-time analysis and the other functions, wherein the functions are executed by a processor executing programming instructions stored in the memory. As described elsewhere herein, in various embodiments, the sensor device 10 includes a PoE power interface, or other power source, and regulator delivering 5 VDC for system operation. This can be further sub-regulated to 3.3 VDC and 1.8 VDC for certain components.

In various embodiments, programming stored in memory causes the processor of the controller to receive monitoring data from one or more of a group of sensor devices 10, and this monitoring data can include data from the particle detection sensor 24 and optionally the gas detection sensor 44. Upon at least a portion of the received monitoring data being indicative of a sufficient match quality, a detected event notification can be transmitted by the controller 20 or by the computing device 55. The received monitoring data measures and reflects the responses of one or more of the group of sensors to one or more specific substances in an environment. In various embodiments, the received monitoring data from the particle detection sensor can be merged with the received monitoring data from the gas detection sensor to more accurately detect specific substances.

In various embodiments, a web-based user interface (e.g., associated with computing device 55) provides various functionality, including allowing a user to configure basic settings for the sensor device(s) 10 using typical web browser software and monitor alerts and detected events.

Alerts (i.e., detected event notifications) can comprise data delivered to or by the computing device 55 in a timely manner. Such data can be the result of the output of rules or processes within the sensor device 10 or computing device 55 that may involve a value or sensed behavior crossing a preset threshold and/or a value or sensed behavior showing a level of match quality, as shown and described elsewhere herein. Alerts can be transmitted as small snippets of XML or JSON, which are pushed by a device to an accessible web service available via network 45. Alert transmissions can be provided for timely warning and alarm messages which are expected only infrequently.

It will be appreciated that any particular sensor can have multiple event entries with different settings. For instance, if a sensor device 10 detects a first level of vaping activity, a notification (i.e., detected event notification) may be sent to a video monitoring system, whereas if the sensor device 10 detects a second level of vaping activity, a notification such as a text or e-mail may be sent to a person of authority via a computing device. A detected event notification can also be an instruction for a suitable device such as a speaker on or remote from sensor device 10 to emit a sound such as a chirp, beep or alarm sound. A detected event notification can also be an instruction to trip a relay, for example, or an instruction for a suitable device including the sensor device 10 to activate a display and/or a light (e.g., LED) to illuminate and/or flash.

It will be appreciated that the present disclosure contemplates several different methods of transmitting such alerts/detected event messages, including, but not limited to, external system native APIs, a REST interface, MQTT or wired connections. As described elsewhere herein, wired electrical bus connections may include CANBUS, MODBUS, RS-485, and others for wired connections to outside data sources and for direct signaling to external related systems such as HVAC controls, building management and automation systems and others. In various embodiments, a single LED 65 is provided to display various system conditions and events, as described above. The LED can display a wide range of colors and illumination patterns. These colors and illumination patterns can be controlled by a separate subsystem which is in turned controlled by the central processor using the I2C bus. This arrangement allows the display of various colors and patterns without burdening the processor with their creation.

In various embodiments, the presently disclosed system provides multiple user interfaces, accessible, for example, at a URL assigned to each sensor device 10. It will be appreciated that there may be a hard-coded default URL and credentials may be provided that make it possible to configure basic settings from a browser operable via any suitable communications device over network 45. Various pages of information can be provided via the user interface(s).

In various embodiments, the sensor device 10 can be connected to a cloud-based program where the generation and dissemination of alerts/detected events communications is performed. A multitude of sensor devices 10 according to the present disclosure can be displayed on a map or building location to provide their absolute GPS location or relative location on a building floor plan. The results from these multitude of devices can be used to generate heat maps of problematic areas as determined by the location determining features of the present disclosure and to generate alerts/detected event notifications based upon the heat map. Video recordings as described elsewhere herein can be initiated and, in various embodiments, may invoke a static or moving camera such as carried on an aerial vehicle (e.g., drone) to capture video of an environment for potential suspect detection, deterrence and/or capture operations. It will be appreciated that the sensor device can be securely configured and monitored via a cloud-based portal, which may be hosted by a third party, for example. Connections to the portal can be established via HTTPS. Administrators can edit device settings, define sensor thresholds and create and edit event rules to trigger other applications and devices. Account settings control groups, individual users and permissions to define who has access to the portal account.

In embodiments incorporating cloud-based operations and other embodiments, it will be appreciated that the processor need not be placed or secured within the sensor device 10. For example, raw sensor data collected via the sensor device 10 as described herein can be transmitted to the cloud-based portal and the processing and subsequent actions can thereby be performed remotely.

Thus, regardless of the location of the processor, the system can operate so as to receive data from the one or more sensors, process the data as described herein and if a suitable match for a profile has been met, trigger appropriate actions, such as alerts, communications and other actions as described herein. The system can further learn from and improve operations via a learning and/or neural network as described elsewhere herein. The system can also operate to time and schedule alerts, and store sensor data and alerts in a database as described herein. Such processing operations can occur in the sensor driver software and circuitry directly associated with each sensor, in the local microprocessor within the housing, in a local gateway device that serves multiple sensors devices, in the "cloud" server that supports a larger number of devices and/or in the user's application (e.g., mobile communications device application) that displays the data.

In various embodiments, the firmware implements a learning mode where the algorithm or other self-learning topology is "programmed" by learning what the sensor readings look like for a normal room or location without pollutants. In various embodiments, this setup is all that is required. Anything that does not "seem" like normal conditions is an alert.

The above-described embodiments of the present disclosure may be implemented in accordance with or in conjunction with one or more of a variety of different types of systems, such as, but not limited to, those described elsewhere herein.

The present disclosure contemplates a variety of different systems each having one or more of a plurality of different features, attributes, or characteristics. A "system" as used herein can refer, for example, to various configurations of: (a) one or more sensor devices; (b) one or more sensor devices and one or more external computing devices; (c) one or more sensor devices communicating via one or more networks; (d) one or more sensor devices and one or more external computing devices communicating via one or more networks; and (e) one or more personal computing devices, such as desktop computers, laptop computers, tablet computers, personal digital assistants, mobile phones, and other mobile computing devices. A system as used herein can also include one or more sensor units and a gateway device designed to capture and amalgamate the information from connected sensor units and transmit this information over a more general or public network with increased efficiency and security. This gateway can also act as a management tool and a sensor health monitor for a group of sensor units, for example.

In certain embodiments in which the system includes a personal computing device in combination with a sensor device, the computing device is any suitable computing device (such as a server) that includes at least one processor and at least one memory device or data storage device. As further described herein, the personal computing device includes at least one processor configured to transmit and receive data or signals representing events, messages, commands, or any other suitable information between the personal computing device and the sensor device. The processor of the personal computing device is configured to execute the events, messages, or commands represented by such data or signals in conjunction with the operation of the personal computing device. Moreover, the processor of the sensor device is configured to transmit and receive data or signals representing events, messages, commands, or any other suitable information between the sensor device and the personal computing device. The processor of the sensor device host is configured to execute the events, messages, or commands represented by such data or signals in conjunction with the operation of the sensor device.

In operation, the sensor device 10 can be installed and can require a wired network connection (Ethernet) which includes standard 802.3af PoE power. In various embodiments, this connection should not be longer than 300 feet (100 M). The sensor device 10 is preferably located on a ceiling or high on a wall to limit casual access. Further, the device 10 can be located in an area relatively free of air currents and areas with significant background noise or vibration, unless circumstances dictate otherwise. The network cable is plugged into a jack such as an RJ-45 jack on the face 30 of the case 15. Programming provided with the sensor device 10 can be employed to find the unit being installed on the network and change the unit's network configuration in accordance with the facility network plan.

In embodiments in which the system includes a computing device (e.g., 55) configured to communicate with a sensor device 10 through a data network (e.g., 45 in FIG. 1), the data network is a local area network (LAN), a wide area network (WAN), a public network such as the Internet, or a private network. The sensor device 10 and the computing device (e.g., 55) are configured to connect to the data network or remote communications link in any suitable manner. In various embodiments, such a connection is accomplished via: a conventional phone line or other data transmission line, a digital subscriber line (DSL), a T-1 line, a coaxial cable, a fiber optic cable, a wireless or wired routing device, a mobile communications network connection (such as a cellular network or mobile Internet network), or any other suitable medium.

It will be appreciated that any combination of one or more computer readable media may be utilized. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing, including a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

As will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, microcode, etc.) or combining software and hardware implementation that may all generally be referred to herein as a "circuit," "module," "component," or "system." Furthermore, aspects of the present disclosure may take the form of a computer program product embodied in one or more computer readable media having computer readable program code embodied thereon.

It will be appreciated that all of the disclosed methods and procedures herein can be implemented using one or more computer programs or components. These components may be provided as a series of computer instructions on any conventional computer-readable medium, including RAM, SATA DOM, or other storage media. The instructions may be configured to be executed by one or more processors which, when executing the series of computer instructions, performs or facilitates the performance of all or part of the disclosed methods and procedures.

Unless otherwise stated, devices or components of the present disclosure that are in communication with each other do not need to be in continuous communication with each other. Further, devices or components in communication with other devices or components can communicate directly or indirectly through one or more intermediate devices, components or other intermediaries. Further, descriptions of embodiments of the present disclosure herein wherein several devices and/or components are described as being in communication with one another does not imply that all such components are required, or that each of the disclosed components must communicate with every other component. In addition, while algorithms, process steps and/or method steps may be described in a sequential order, such approaches can be configured to work in different orders. In other words, any ordering of steps described herein does not, standing alone, dictate that the steps be performed in that order. The steps associated with methods and/or processes as described herein can be performed in any order practical. Additionally, some steps can be performed simultaneously or substantially simultaneously despite being described or implied as occurring non-simultaneously.

It will be appreciated that algorithms, method steps and process steps described herein can be implemented by appropriately programmed computers and computing devices, for example. In this regard, a processor (e.g., a microprocessor or controller device) receives instructions from a memory or like storage device that contains and/or stores the instructions, and the processor executes those instructions, thereby performing a process defined by those instructions. Furthermore, aspects of the present disclosure may take the form of a computer program product embodied in one or more computer readable media having computer readable program code embodied thereon.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on a user's computer, partly on a user's computer, as a stand-alone software package, partly on a user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS). It will be appreciated that the computer code may also be implemented using an RTOS (real time operating system) together with appropriate application code to provide a more timely response capability.

Where databases are described in the present disclosure, it will be appreciated that alternative database structures to those described, as well as other memory structures besides databases may be readily employed. The drawing figure representations and accompanying descriptions of any exemplary databases presented herein are illustrative and not restrictive arrangements for stored representations of data. Further, any exemplary entries of tables, charts, graphs and parameter data represent example information only, and, despite any depiction of the databases as tables, other formats (including relational databases, object-based models and/or distributed databases) can be used to store, process and otherwise manipulate the data types described herein. Electronic storage can be local or remote storage, as will be understood to those skilled in the art. Appropriate encryption and other security methodologies can also be employed by the system of the present disclosure, as will be understood to one of ordinary skill in the art.

The invention claimed is:

1. A device, comprising;
a particle detection sensor operable to detect a range of particle measurements in each of a plurality of bins, wherein a first bin of the plurality of bins measures a first particle measurement value for particles of a first size, and wherein a second bin of the plurality of bins measures a second particle measurement value for particles of a second size, wherein the second size is larger than the first size;
a processor;
a memory storing instructions that, when executed by the processor, cause the processor to:
generate a first sample histogram comprising particle measurement values in each of the plurality of bins, wherein the first sample histogram represents an ambient environment being evaluated and comprises the first and second particle measurement values as received from the particle detection sensor at a first time;
generate a second sample histogram comprising particle measurement values in each of the plurality of bins, wherein the second sample histogram comprises the first and second particle measurement values as received from the particle detection sensor at a second time different from the first time;
determine a distance of a source of a pollutant from the device based upon the first and second sample histograms;
determine, based on a comparison of the first sample histogram with a profile histogram, a match quality value for the presence of the pollutant in the environment;
upon the match quality value meeting or exceeding a threshold match value, generate a detected event notification.

2. The device of claim 1, wherein the range of particle measurements comprises a range of particle mass concentrations, wherein the first particle measurement value comprises a first particle mass concentration and wherein the second particle measurement value comprises a second particle mass concentration.

3. The device of claim 2, wherein the range of particle measurements further comprises a range of particle counts, wherein the first particle measurement value further comprises a first particle count, wherein the second particle measurement value further comprises a second particle count; and wherein the match quality value comprises a first match quality value associated with the first and second particle mass concentrations and a second match quality value associated with the first and second particle counts.

4. The device of claim 1, wherein the range of particle measurements comprises a range of particle counts, wherein the first particle measurement value comprises a first particle count and wherein the second particle measurement value comprises a second particle count.

5. The device of claim 1, wherein the match quality value is determined based on whether the first particle measurement value fits between a value range in the profile histogram for the first bin and whether the second particle measurement value fits between a value range in the profile histogram for the second bin.

6. The device of claim 1, wherein the match quality value is determined based on the degree to which the first particle measurement value fits between a value range in the profile histogram for the first bin and the degree to which the second particle measurement value fits between a value range in the profile histogram for the second bin.

7. The device of claim 1, wherein the first and second particle measurement values of the first sample histogram are measured at a plurality of intervals over a time span, and wherein the match quality value is determined based on the highest degree to which the first particle measurement value as measured at the plurality of intervals fits between a value range in the profile histogram for the first bin and based on the highest degree to which the second particle measurement value as measured at the plurality of intervals fits between a value range in the profile histogram for the second bin.

8. The device of claim 1, wherein the first and second particle measurement values of the first sample histogram are measured at a plurality of intervals over a time span, and wherein the match quality value is determined based on the average degree to which the first particle measurement value as measured at the plurality of intervals fits between a value range in the profile histogram for the first bin and based on the average degree to which the second particle measurement value as measured at the plurality of intervals fits between a value range in the profile histogram for the second bin.

9. The device of claim 1, wherein the match quality value is determined based on whether the first particle measurement value does not fit between a value range in the profile histogram for the first bin or whether the second particle measurement value does not fit between a value range in the profile histogram for the second bin.

10. The device of claim 1, further comprising a gas sensor operable to measure at least one gas, and wherein the detected event notification further comprises a measurement of at least one gas as received by the gas sensor.

11. The device of claim 1, further comprising a gas sensor operable to measure at least one gas, and wherein the array of the first sample histogram comprises a measurement of at least one gas as received by the gas sensor.

12. The device of claim 1, wherein the profile histogram comprises a first bin range of high and low particle measurement values corresponding to the presence of the pollutant in the environment and a second bin range of high and low particle measurement values corresponding to the presence of the pollutant in the environment.

13. The device of claim 1, wherein the pollutant is vape or smoke.

14. A system, comprising:
a plurality of networked particle detection sensors, each of which is operable to detect a range of particle measurements in each of a plurality of bins, wherein a first bin of the plurality of bins for each of the plurality of particle detection sensors measures a first particle measurement value for particles of a first size, and wherein a second bin of the plurality of bins for each of the plurality of particle detection sensors measures a second particle measurement value for particles of a second size, wherein the second size is larger than the first size;

a processor;

a memory storing instructions that, when executed by the processor, cause the processor to:

generate a series of first sample histograms comprising an array of particle measurement values in each of the plurality of bins for each of the plurality of particle detection sensors, wherein the series of first sample histograms represents an ambient environment being evaluated, wherein the array for each of the plurality of particle detection sensors comprises the first and second particle measurement values as received from each of the plurality of particle detection sensors;

determine a distance of each of the plurality of particle detection sensors to a source of a pollutant within the environment based upon sensor measurement values consisting of the particle measurement values in each of the plurality of bins over a time span;

determine, based on a comparison of the series of first sample histograms with a profile histogram, a match quality value for each of the plurality of particle detection sensors for the presence of the pollutant in the environment; and upon the match quality value for at least one of the plurality of particle detection sensors meeting or exceeding a threshold match value, generate a detected event notification.

15. The system of claim 14, wherein each of the plurality of networked particle detection sensors is positioned at an independent location in an environment, and wherein the instructions further cause the process to determine, based on the match quality value for each of the plurality of particle detection sensors, a relative proximity of each of the plurality of particle detection sensors to a source of the pollutant within the environment.

16. The system of claim 14, wherein the range of particle measurements comprises a range of particle mass concentrations, wherein the first particle measurement value comprises a first particle mass concentration and wherein the second particle measurement value comprises a second particle mass concentration.

17. The system of claim 16, wherein the range of particle measurements further comprises a range of particle counts, wherein the first particle measurement value further comprises a first particle count, wherein the second particle measurement value further comprises a second particle count; and wherein the match quality value comprises a first match quality value associated with the first and second particle mass concentrations and a second match quality value associated with the first and second particle counts.

18. The system of claim 14, wherein the range of particle measurements comprises a range of particle counts, wherein the first particle measurement value comprises a first particle count and wherein the second particle measurement value comprises a second particle count.

19. The system of claim 14, wherein the match quality value is determined based on whether the first particle measurement value fits between a value range in the profile histogram for the first bin and whether the second particle measurement value fits between a value range in the profile histogram for the second bin.

20. The system of claim 14, wherein the match quality value is determined based on the degree to which the first particle measurement value fits between a value range in the profile histogram for the first bin and the degree to which the second particle measurement value fits between a value range in the profile histogram for the second bin.

21. The system of claim 14, wherein the first and second particle measurement values of the first sample histogram are measured at a plurality of intervals over a time span, and wherein the match quality value is determined based on the highest degree to which the first particle measurement value as measured at the plurality of intervals fits between a value range in the profile histogram for the first bin and based on the highest degree to which the second particle measurement value as measured at the plurality of intervals fits between a value range in the profile histogram for the second bin.

22. The system of claim 14, wherein the first and second particle measurement values of the first sample histogram are measured at a plurality of intervals over a time span, and wherein the match quality value is determined based on the average degree to which the first particle measurement value as measured at the plurality of intervals fits between a value range in the profile histogram for the first bin and based on the average degree to which the second particle measurement value as measured at the plurality of intervals fits between a value range in the profile histogram for the second bin.

23. The system of claim 14, wherein the match quality value is determined based on whether the first particle measurement value does not fit between a value range in the profile histogram for the first bin or whether the second particle measurement value does not fit between a value range in the profile histogram for the second bin.

24. The system of claim 14, further comprising a gas sensor operable to measure at least one gas, and wherein the detected event notification further comprises a measurement of at least one gas as received by the gas sensor.

25. The system of claim 14, further comprising a gas sensor operable to measure at least one gas, and wherein the array of the first sample histogram comprises a measurement of at least one gas as received by the gas sensor.

26. The system of claim 14, wherein the profile histogram comprises a first bin range of high and low particle measurement values corresponding to the presence of the pollutant in the environment and a second bin range of high and low particle measurement values corresponding to the presence of the pollutant in the environment.

27. The system of claim 14, wherein the pollutant is vape or smoke.

28. A computer-implemented method, comprising:

receiving, by a computing device, first and second particle measurement values as received from a particle detection sensor, wherein the particle detection sensor is operable to detect a range of particle measurements in each of a plurality of bins, wherein a first bin of the plurality of bins measures a first particle measurement value for particles of a first size, and wherein a second bin of the plurality of bins measures a second particle measurement value for particles of a second size, wherein the second size is larger than the first size, wherein the first and second particle measurement values of the first sample histogram are measured at a plurality of intervals over a time span;

generate, by the computing device based on the received first and second particle measurement values, a first sample histogram comprising an array of particle measurement values in each of the plurality of bins, wherein the first sample histogram represents an ambient environment being evaluated;

determine a distance of a source of the pollutant from the device based solely upon the first and second particle measurement values over the time span;

determine, based on a comparison of the first sample histogram with a profile histogram, a match quality value for the presence of a pollutant in the environment; and upon the match quality value meeting or exceeding a threshold match value, generate a detected event notification.

* * * * *